United States Patent [19]

Hoelderich et al.

[11] Patent Number: 4,866,210
[45] Date of Patent: Sep. 12, 1989

[54] PREPARATION OF KETONES

[75] Inventors: Wolfgang Hoelderich, Frankenthal; Leopold Hupfer, Friedelsheim; Kurt Schneider, Bad Durkheim, all of Fed. Rep. of Germany

[73] Assignee: BASF Aktiengesellschaft, Ludwigshafen, Fed. Rep. of Germany

[21] Appl. No.: 144,372

[22] Filed: Jan. 15, 1988

[30] Foreign Application Priority Data

Jan. 28, 1987 [DE] Fed. Rep. of Germany ....... 3702483

[51] Int. Cl.[4] .............................. C07C 45/65
[52] U.S. Cl. .................... 568/392; 568/347; 568/315; 568/396; 568/346; 568/314
[58] Field of Search ............ 568/392, 347, 315, 396, 568/346, 415, 314

[56] References Cited

U.S. PATENT DOCUMENTS

| | | | |
|---|---|---|---|
| 2,312,751 | 3/1943 | Cohen | 568/392 |
| 2,371,577 | 3/1945 | Hall et al. | 568/392 |
| 2,802,876 | 8/1957 | Broich et al. | 568/392 |
| 2,913,497 | 11/1959 | Grimme et al. | 568/392 |
| 3,405,178 | 10/1968 | Wollner et al. | 568/396 |
| 3,890,392 | 6/1975 | Ember | 568/392 |
| 3,953,517 | 4/1976 | Schmitt et al. | 568/396 |
| 4,339,606 | 7/1982 | Huang et al. | 568/396 |
| 4,701,562 | 10/1987 | Olson | 568/390 |

FOREIGN PATENT DOCUMENTS

| | | | |
|---|---|---|---|
| 658801 | 7/1965 | Belgium | 568/315 |
| 2758113 | 5/1965 | Fed. Rep. of Germany | 568/315 |
| 47-15810 | 5/1972 | Japan | 568/396 |
| 48-33724 | 10/1973 | Japan | 568/396 |
| 61-56147 | 3/1986 | Japan | 568/347 |
| 745946 | 3/1956 | United Kingdom | 568/392 |
| 762421 | 11/1956 | United Kingdom | 568/392 |
| 993389 | 7/1979 | United Kingdom | 568/315 |

OTHER PUBLICATIONS

Sumitomo Chemical Industries, Chem. Abstract, vol. 105, No. 1, p. 579 (1986).
European Search Report.

Primary Examiner—James H. Reamer
Attorney, Agent, or Firm—Keil & Weinkauf

[57] ABSTRACT

Ketones of the formula

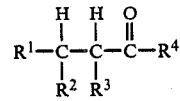

where $R^1$ to $R^3$ are each hydrogen and $R^1$ to $R^4$ are each alkyl of 1 to 12 carbon atoms, cycloalkyl of 4 to 8 carbon atoms, aryl, aralkyl or alkylaryl, which each in turn may be substituted, or $R^1$ and $R^2$ and $R^3$ together with the carbon atoms to which they are bonded form a cycloalkane, are prepared by reacting ketones of the formula

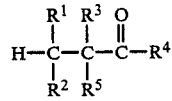

where one of $R^1$, $R^2$, $R^3$ and $R^5$ is hydroxyl, alkoxy or carboxyl while the remaining $R^1$ to $R^4$ have the above-mentioned meanings, with hydrogen in the presence of acid catalysts supporting one or more hydrogenation components, zeolites of the pentasil type being particularly suitable.

4 Claims, No Drawings

PREPARATION OF KETONES

The present invention relates to a process for preparing a ketone by dehydration and simultaneous hydrogenation in the presence of an acid catalyst.

Ketones are much sought-after chemical compounds on account of their many possible uses in the preparation of a very wide range of products.

In particular in the industrial production of asymmetrically substituted ketones it is generally necessary to resort to the condensation of different organic acids with decarboxylation, as described for example in German Laid-Open Application DOS 2,758,113. With this process, the production of symmetrically substituted ketones and carbon dioxide is a disadvantage.

It is also possible to hydrogenate unsaturated ketones in a conventional manner. For instance, it is known to prepare alpha, beta-unsaturated ketones by aldol condensation of aliphatic ketones and formaldehyde in the presence of oxalic acid or in the presence of cation exchangers and $H_2O$ under superatmospheric pressure (GB Patent 993,389) or by reaction of enol acetates with ketones in the presence of Lewis acids, such as $BF_3$ or $TiCl_4$, or by oxidation of branched olefins in 50% strength acetic acid and in the presence of $PdCl_2$ as catalyst (BE Patent 658,801), or by condensation of saturated carbonyl compounds in the presence of $BF_3$. There is also a multistage process where alpha, betaunsaturated ketones are obtained by condensation of ketones in the presence of tosylmethyl isocyanide, subsequent alkylation and hydrolysis. Other complicated methods of preparation are for example the ozonolysis of 2,3-dimethylbutadienes or the anodic oxidation of beta-ketocarboxylates, or the photoisomerization of 1,2-diacylcyclobutanes. The gas phase oxidation of olefins over metal oxide/phosphorus oxide catalysts leads aselectively to a mixture of various compounds, including alpha, beta-unsaturated ketones. These processes for preparing unsaturated ketones have various disadvantages, namely starting compounds which are difficult to obtain, toxic and corrosive homogeneous catalysts, or energyconsuming or multistage reactions, such as ozonolysis and photoisomerization.

A disadvantage of the preparation of saturated ketones from precursors of unsaturated ketones is the two-stage procedure where the unsaturated ketones are obtained in the first stage and hydrogenated in the second stage.

It is an object of the present invention to synthesize saturated ketones, in particular asymmetrically substituted ketones, by simple reaction from readily accessible starting compounds.

We have found that this object is achieved in a process for preparing an in particular asymmetrically substituted ketone of the formula (I)

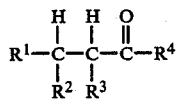

where $R^1$ to $R^4$ are each alkyl of 1 to 12 carbon atoms, cycloalkyl of 4 to 8 carbon atoms, aryl, aralkyl or alkyl, which each in turn may be substituted, or $R^1$ and $R^2$ or $R^2$ and $R^3$ together with the carbon atoms to which they are bonded can form a cycloalkane, by dehydration and hydrogenation in a single step with high selectivities, conversions and catalyst lives by reacting a ketone of the formula II

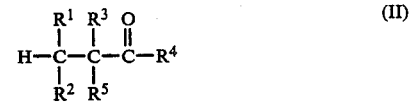

where one of $R^1$, $R^2$, $R^3$ and $R^5$ is hydroxyl, alkoxy or carboxyl while the remaining $R^1$ to $R^4$ each have the abovementioned meanings, with hydrogen in the presence of an acid catalyst supporting one or more hydrogenation components.

Ketones of the formula (II) which can be used as starting materials according to the invention are for example 3-methyl-3-hydroxybutan-2-one, 3-methyl-3-hydroxypentan-2-one, 3-pentamethylene-3-hydroxypropan-2-one and also 3-methyl-3-hydroxyheptan-2-one and 3-phenyl-3-hydroxy-3-methylpropan-2-one. The starting materials are preparable from tert-acetyl alcohols by the procedure described for example in DE Patent 1,129,941.

For instance, by the process of the invention 3-methyl-3-hydroxybutan-2-one, for example, is converted by elimination of $H_2O$ and introduction of $H_2$ into methyl isopropyl ketone.

The acid catalyst with hydrogenation component used in the process according to the invention is preferably a zeolite, advantageously in the acidic form. Zeolites are crystalline aluminosilicates which have a highly ordered structure comprising a rigid three-dimensional network of $SiO_4$ and $AlO_4$ tetrahedra linked by common oxygen atoms. The ratio of the Si and Al atoms:oxygen is 1:2. The electrovalence of the aluminum-containing tetrahedra is balanced by the inclusion in the crystal of cations, for example an alkali metal or hydrogen ion. Cation exchange is possible. The spaces between the tetrahedra are occupied by water molecules prior to dehydration through drying or calcination.

In the zeolites, the aluminum in the lattice can be replaced by other elements such as B, Ga, Fe, Cr, V, As, Sb, Bi or Be or mixtures thereof, or the silicon can be replaced by a tetravalent element such as Ge, Ti, Zr or Hf.

According to their structure, zeolites are divided into various groups. For instance, the zeolite structure is formed in the mordenite group by tetrahedra arranged in chains and in the chabasite group of tetrahedra arranged in layers, while in the faujasite group the tetrahedra form polyhedra, for example in the form of a cuboctahedron which is composed of tetragons and hexagons. Depending on the way the cuboctahedra are linked, which produces differently sized voids and pores, zeolites are classed as type A, L, X or Y.

Catalysts suitable for the process according to the invention are zeolites from the mordenite group or narrow-pored zeolites of the erionite or chabasite type or zeolites of the faujasite type, for example Y-, X- or L-zeolites.

This group of zeolites also includes the ultrastable zeolites of the faujasite type, ie. dealuminized zeolites. Methods for preparing such zeolites have repeatedly been described.

Zeolites of the pentasil type are particularly advantageous. Their common feature is a pentagon composed of $SiO_4$ tetrahedra. They are characterized by a high $SiO_2/Al_2O_3$ ratio and by pore sizes between those of the zeolites of type A and those of type X or Y.

These zeolites can have different chemical compositions. They can be aluminosilicate, borosilicate or iron, beryllium, gallium, chromium, arsenic, antimony or bismuth silicate zeolites or mixtures thereof and aluminogermanate, borogermanate and gallium or iron germanate zeolites or mixtures thereof. Particularly suitable for the process according to the invention are the aluminosilicate, borosilicate and iron silicate zeolites of the pentasil type. The aluminosilicate zeolite is prepared for example from an aluminum compound, preferably $Al(OH)_3$ or $Al_2(SO_4)_3$, and a silicon component, preferably finely divided silicon dioxide in an aqueous amine solution, in particular in polyamines such as 1,6-hexanediamine or 1,3-propanediamine or triethylenetetramine solution, in the presence or in particular in the absence of alkali metal or alkaline earth metal at from 100° to 220° C. under autogenous pressure. This also includes the isotactic zeolites described in EP 34,727 and EP 46,504. The alumino-silicate zeolites obtained have an $SiO_2/Al_2O_3$ ratio of from 10 to 40,000, depending on the mixing ratio of the starting materials. These aluminosilicate zeolites of the pentasil type can also be synthesized in an ether medium such as diethylene glycol dimethyl ether, in an alcohol medium such as methanol or 1,4-butanediol, or in water.

The high-silicon zeolites usable according to the invention ($SiO_2/Al_2O_3 \geq 10$) also include the various ZSM types, ferrierite, Nu-1 and Silicalit ®.

Borosilicate zeolites can be synthesized under autogenous pressure, for example at from 90 to 200° C., by reacting a boron compound, for example $H_3BO_3$, with a silicon compound, preferably finely divided silicon dioxide, in an aqueous amine solution, in particular in 1,6-hexanediamine, 1,3-propanediamine or triethylenetetramine solution, in the presence or in particular in the absence of alkali metal or alkaline earth metal. They also include the isotactic zeolites described in EP 34,727 and EP 46,504. These borosilicate zeolites can also be prepared by carrying out the reaction not in aqueous amine solution but in an ether solution, for example diethylene glycol dimethyl ether, or in an alcohol solution, for example 1,6-hexanediol.

The iron silicate zeolite is obtained for example from an iron compound, preferably $Fe_2(SO_4)_3$, and a silicon compound, preferably finely divided silicon dioxide in an aqueous amine solution, in particular 1,6-hexanediamine, in the presence or absence of alkali metal or alkaline earth metal at from 100° to 200° C. under autogenous pressure.

The aluminosilicate, borosilicate and iron silicate zeolites thus prepared, after they have been isolated, dried at from 108° to 160° C. and calcined at from 450° to 550° C., preferably at 500° C., can be combined with a binder in a ratio of from 90:10 to 40:60 % by weight and molded into extrudates or tablets. Suitable binders are various aluminum oxides, preferably boehmite, amorphous aluminosilicates having an $SiO_2/Al_2O_3$ ratio of from 25:75 to 90:5, preferably 75:25, silicon dioxide, preferably finely divided $SiO_2$, mixtures of finely divided $SiO_2$ and finely divided $Al_2O_3$, $TiO_2$, $ZrO_2$, and clay. After molding, the extrudates or tablets are dried at 110° C./16 h and calcined at 500° C./16 h.

It is also possible to obtain advantageous catalysts by molding the isolated aluminosilicate or borosilicate zeolite immediately after drying and subjecting it to calcination only after the molding. The aluminosilicate and borosilicate zeolites prepared can be used in the pure form, without binder, as extrudates or tablets, the extrusion or peptization aids used being for example ethylcellulose, stearic acid, potato starch, formic acid, oxalic acid, acetic acid, nitric acid, ammonia, amines, silicoesters and graphite or mixtures thereof.

If the zeolite, on account of its manner of preparation, is present not in the catalytically active, acidic H-form but, for example, in the Na-form, it can be completely or partially converted into the desired H-form by ion exchange, for example with ammonium ions and subsequent calcination, or by treatment with acids.

The hydrogenation component applied to the molded or unmolded zeolite comprises a transition metal, such as Cr, Mo, W, Mn, Re, V, Nb, in particular metals of group 8, such as Fe, Co, Ni, Ru, Rh, Pd, Os, Ir, Pt, and of subgroups I and II, such as Cu, Ag, Zn or mixtures thereof. This doping can be effected by ion exchange or impregnation with metal salts.

Advantageously, doping is carried out by introducing the molded zeolite into a riser pipe and passing an aqueous or ammoniacal solution of a halide or nitrate of one of the abovementioned metals over it at from 20° to 100° C. Such an ion exchange can take place with the hydrogen, ammonium, or alkali metal form of the zeolite. Another way of applying metal to the zeolite comprises impregnating the zeolitic material with, for example, a halide, nitrate or oxide of one of the abovementioned metals in aqueous, alcoholic or ammoniacal solution. Both ion exchange and impregnation are followed by at least a drying step, and optionally by repeated calcination.

A possible embodiment comprises for example dissolving $Cu(NO_3)_2 \times 3$ $H_2O$ or $Ni(NO_3)_2 \times 6$ $H_2O$ or $Ce(NO_3)_3 \times 6$ $H_2O$ or $La(NO_3)_2 \times 6$ $H_2O$ or $Pd(NO_3)_2$ in water and impregnating the molded or unmolded zeolite with this solution for a certain period, for example 30 minutes. Any supernatant solution is stripped of water in a rotary evaporator. The impregnated zeolite is then dried at about 150° C. and calcined at about 550° C. This impregnating step can be carried out several times in succession until the desired metal content is obtained.

It is also possible to prepare an aqueous $Ni(NO_3)_2$ solution or ammoniacal $Pd(NO_3)_2$ solution and to suspend the pure pulverulent zeolite therein at from 40° to 100° C. by stirring for about 24 hours. After filtration, drying at about 150° C. and calcination at about 500° C., the zeolitic material thus obtained can be further processed with or without binders into extrudates, pellets or fluidizable material.

An ion exchange on the zeolite present in the H-form or ammonium form or alkali metal form can be carried out by introducing the zeolite in extruded or pellet form into a column and for example passing an aqueous $Ni(NO_3)_2$ solution or ammoniacal $Pd(NO_3)_2$ solution over it in a recycle loop and at a slightly elevated temperature of from 30° to 80° C. for from 15 to 20 hours. This is followed by washing out with water, drying at about 150° C. and calcination at about 550° C. With some metal-doped zeolites, for example Pd-, Cu- or Ni-doped zeolites, an aftertreatment with hydrogen is advantageous.

In some cases it is also advantageous to reduce the catalyst before the start of the reaction. For example at Pt-, Pd- or Cu-doped zeolite catalyst is heated in a reactor to 170°-220° C. under nitrogen, and hydrogen is then slowly added. A constant temperature is maintained until no further water is formed. The reduction can also be carried out by the method described in J. Catal. 89 (1984), 520-526.

By impregnation and ion exchange it is also possible to apply a plurality of metals simultaneously as hydrogenation components.

To obtain high selectivities, high conversions and long catalyst lives, it is advantageous to modify the zeolites. A suitable method of modifying the catalyst comprises for example doping in addition to the above-mentioned hydrogenation components unmolded or molded zeolites with metal salts by ion exchange or impregnation. The metals used are alkali metals, such as Li, Cs, or K, alkaline earth metals, such as Mg, Ca, Sr or Ba, metals of main groups III, IV and V, such as B, Al, Ga, Ge, Sn, Pb or Bi, and rare earth metals such as La, Ce, Pr, Nd, Er, Yb and U. The modification with these metals can be effected by ion exchange or impregnation simultaneously with the application of a hydrogenation component, or be effected after the hydrogenation component has been applied and, possibly, after a calcination has subsequently been carried out.

A further method of modifying the zeolite comprises treating the zeolitic material, which may be in molded or unmolded form, with an acid such as hydrochloric acid, hydrofluoric acid or phosphoric acid and/or steam. This modifying treatment is then followed by the application of the hydrogenation component.

In detail, for example, the zeolite is treated in pulverulent form with 1 N phosphoric acid at 80° C. for 1 hour and then washing with water, drying at 110° C./16 hours and calcining at 500° C./20 hours. Alternatively, before or after being molded together with a binder, the zeolite is treated for example at from 60° to 80° C. with from 3 to 25% strength by weight, in particular from 12 to 20% strength by weight, aqueous hydrochloric acid for from 1 to 3 hours. Afterwards, the zeolite thus treated is washed with water, dried and calcined at from 400° C. to 500° C. This is followed by the application of the hydrogenation component by ion exchange or impregnation, as described above.

In a particular embodiment, the acid treatment comprises treating the zeolitic material, before it is molded, with hydrofluoric acid, generally in the form of 0.001 N to 2 N, preferably 0.05 N to 0.5 N, hydrofluoric acid, at an elevated temperature, for example by heating under reflux for, in general, from 0.5 to 5, preferably from 1 to 3, hours. After the zeolitic material has been isolated, for example by filtering and washing, it is advantageously dried, for example at from 100° to 160° C., and calcined, in general at from 450° C. to 600° C. In a further preferred form of the acid treatment, the zeolitic material, after it has been molded together with a binder, is treated at an elevated temperature, advantageously at from 50° to 90° C., preferably at from 60° to 80° C., for from 0.5 to 5 hours with, preferably, from 12 to 20 % strength by weight hydrochloric acid. Expediently, the zeolitic material is subsequently washed, dried at from 100° to 160° C. and calcined at from 450° to 600° C. An HF treatment can also be followed by an HCl treatment. Thereafter the hydrogenation component is applied as described above.

Alternatively, zeolites can be modified by applying phosphorus compounds, such as trimethoxy phosphate, trimethoxyphosphine or primary, secondary or tertiary sodium phosphate. The treatment with primary sodium phosphate has proven to be particularly advantageous. In this treatment, the zeolite in the extrudate, tablet or fluidizable form is saturated with aqueous $NaH_2PO_4$ solution, and dried at 110° C. and calcined at 500° C. This is followed by application of the hydrogenation component.

If in the use according to the invention the zeolitic catalyst, like the other catalysts used at the same time, undergoes deactivation due to coking, it is advisable to regenerate by burning off the coke deposit with air or with an air/nitrogen mixture at from 400° to 550° C., preferably 500° C. This restores the zeolite to its initial activity level.

By precoking it is possible to set the activity of a catalyst for optimum selectivity in respect of the desired reaction product.

Further catalysts for preparing ketones are phosphates, in particular aluminum phosphates, silicon aluminum phosphates, silicon iron aluminium phosphates, cerium phosphate, zirconium phosphates, boron phosphate, iron phosphate, strontium phosphate or mixtures thereof.

Suitable aluminum phosphate catalysts for the process according to the invention are in particular aluminum phosphates synthesized under hydrothermal conditions. Examples of suitable aluminum phosphates are APO-5, APO-9, APO-11, APO-12, APO-14, APO-21, APO-25, APO-31 and APO-33.

$AlPO_4$-5 (APO-5), for example, is synthesized by by homogeneously mixing orthophosphoric acid with pseudoboehmite (Catapal SB ®) in water, adding tetrapropylammonium hydroxide to this mixture, and then reacting in an autoclave under autogenous pressure at about 150° C. for from 20 to 60 hours. The $AlPO_4$ is filtered off, dried at from 100° to 160° C. and calcined at from 450° to 550° C.

$AlPO_4$-9 (APO-9) is likewise synthesized from orthophosphoric acid and pseudoboehmite, but in aqueous DABCO solution (1,4-diazabicyclo(2,2,2)octane) at about 200° C. under autogeneous pressure in the course of from 200 to 400 hours. If ethylenediamine is used in place of DABCO solution, APO-12 is obtained.

The synthesis of $AlPO_4$-21 (APO-21) is effected from orthophosphoric acid and pseudoboehmite in aqueous pyrrolidine solution at from 150° to 200° C. under autogenous pressure in the course of from 50 to 200 hours.

The process according to the invention can also be carried out with known silicon aluminum phosphates such as SAPO-5, SAPO-11, SAPO-31 and SAPO-34. These compounds are prepared by crystallization from aqueous mixture at from 100° to 250° C. and under autogenous pressure in the course of from 2 hours to 2 weeks, the reaction mixture, comprising a silicon, an aluminum and a phosphorus component, being converted in an aqueous organoamine-containing solution.

SAPO-5, for example, is obtained by mixing $SiO_2$, suspended in an aqueous tetrapropylammonium hydroxide solution, with an aqueous suspension of pseudoboehmite and orthophosphoric acid and then reacting at from 150° to 200° C. under autogenous pressure in a stirred autoclave for from 20 to 200 hours. The powder is filtered off, dried at from 110° to 160° C. and calcined at from 450° to 550° C.

Suitable silicon aluminum phosphates also include ZYT-5, ZYT-6, ZYT-7, ZYT-9, ZYT-11 and ZYT-12.

The phosphate catalyst used in the process can be a precipitated aluminum phosphate. For example, such an aluminum phosphate is prepared by dissolving 92 g of diammonium hydrogenphosphate in 700 ml of water. 260 g of $Al(NO_3)_3 \times H_2O$ in 700 ml of water are added dropwise to this solution in the course of 2 hours, during which pH 8 is maintained by adding 25% strength NH$_3$ solution at the same time. The resulting precipitate is subsequently stirred for 12 hours and then filtered off with suction and washed. It is dried at 60° C./16 h.

A boron phosphate catalyst for use in the process according to the invention can be prepared for example by mixing and kneading concentrated boric acid and phosphoric acid and subsequently drying and calcining in an inert gas, air or vapor atmosphere at from 250° to 650° C., preferably at from 300° to 500° C.

To these phosphates are applied the hydrogenation components as described above, by impregnation (soaking and spraying) or in some cases even by ion exchange. It is also possible, as with the zeolite catalysts, to carry out a modification with metals or acids.

Suitable acid catalysts also include for example the acidic oxides of elements of main groups III and IV and of subgroups IV to VI of the periodic table, in particular oxides, such as silicon dioxide, in the form of silica gel, diatomaceous earth or quartz, and also titanium dioxide, zirconium dioxide, phosphorus oxides, vanadium pentoxide, niobium oxide, boron trioxide, aluminum oxide, chromium oxide, molybdenum oxides, tungsten oxides or mixtures thereof. This too is followed by the application of the hydrogenation component, and a modification with metals or acids is possible beforehand or afterwards.

It is also possible to use catalysts impregnated with phosphoric acid or boric acid. Phosphoric acid or boric acid is applied to SiO$_2$, Al$_2$O$_3$ or pumice carriers, for example by soaking or spraying. A catalyst containing phosphoric acid can be obtained for example by impregnating SiO$_2$ with H$_3$PO$_4$ or NaH$_2$PO$_4$ solution and subsequent drying or calcination. However, phosphoric acid can also be sprayed together with silica gel in a spray tower; this is followed by drying and usually calcination. Phosphoric acid can also be sprayed onto the carrier material in an impregnating mill. The hydrogenation component is applied thereafter.

The catalysts described here can optionally be used in the form of from 2 to 4 mm extrudates or as tablets from 3 to 5 mm in diameter or as chips having particle sizes from 0.1 to 0.5 mm, or in a fluidizable form.

The reaction conditions generally chosen for reacting the hydroxy-, alkoxy- or carboxy-ketones according to the invention are in the preferred gas phase at from 100° to 500° C., for example 150° to 450° C., and in particular from 300° to 400° C., operating at a weight hourly space velocity (WHSV) from 0.1 to 20 h$^{-1}$, in particular from 1.0 to 10.0$^{-1}$, g of starting material per g of catalyst per hour.

The ratio hydrogen:ketone ranges from 1:1 to 100:1 moles, in particular from 3:1 to 30:1 moles.

The gas phase reaction can be carried out in a fixed bed or in a fluidized bed.

It is also possible to carry out the reaction in the liquid phase (by the suspension, trickle bed or liquid phase procedure) at from 50° to 200° C.

The process is generally carried out under atmospheric pressure or, depending on the volatility of the starting compound, under reduced or superatmospheric pressure, batchwise or preferably continuously.

Sparingly volatile solid starting materials are used in dissolved form, for example in solution in THF, toluene or petroleum ether. It is also possible to dilute the starting material with the solvents or with inert gases, such as N$_2$, Ar or H$_2$O vapor.

After the reaction, the resulting products are isolated from the reaction mixture in a conventional manner, for example by distillation; unconverted starting materials are, if appropriate, recycled into the reaction.

EXAMPLES 1 TO 10

The reaction is carried out under isothermal conditions in the gas phase in a tubular reactor (helix, internal diameter 0.6 cm, length 90 cm) for not less than 6 hours. The reaction products are separated off and characterized in a conventional manner. Quantitative determination of the reaction products and of the starting materials is by gas chromatography.

The catalysts used in the Examples are:

Catalyst A

A borosilicate zeolite of the pentasil type is prepared in a hydrothermal synthesis at autogenous pressure at 170° C. in a stirred autoclave from 640 g of finely divided SiO$_2$, 122 g of H$_3$BO$_3$, 8,000 g of an aqueous 1,6-diaminohexane solution (mixture 50:50% by weight). After filtering and washing, the crystalline reaction product is dried at 100° C./24 h and calcined at 500° C./24 h. This borosilicate zeolite comprises 94.2% by weight of SiO$_2$ and 2.3% by weight of B$_2$O$_3$. This material is molded with a molding aid into 2 mm extrudates which are dried at 110° C./16 h and calcined at 500° C./24 h.

Catalyst A is obtained by impregnating these extrudates with an aqueous Cu(NO$_3$)$_2$ solution, drying at 130° C./2 h and calcining at 540° C./2 h. The Cu content is 3.4% by weight.

Catalyst B

Catalyst B is prepared like catalyst A, except that the Cu(NO$_3$)$_2$ solution is replaced aqueous Pd(NO$_3$)$_2$ solution. The Pd content is 1.4% by weight.

Catalyst C

The borosilicate zeolite extrudates as described in the case of catalyst A are introduced into a column and subjected to ion exchange at 50° C. with an ammoniacal palladium nitrate solution. Washing with H$_2$O is followed by drying at 110° C. and calcination at 500° C./5 h. The Pd content is 1.9% by weight.

Catalyst D

Catalyst D is prepared like catalyst A, except that the Cu-nitrate is replaced by an aqueous solution of Pd- and Ce-nitrate. The Pd content is 0.47% by weight and the Ce content 2.3% by weight.

Catalyst E

Catalyst E is prepared like catalyst D. The Pd content is 1.3% by weight and the Ce content 3.6% by weight.

Catalyst F

Catalyst F is prepared like catalyst D, except that it is impregnated with an aqueous solution of Pd-and Pr-nitrate. The Pd content is 1% by weight, and the PrO$_2$ content 4.6% by weight.

Catalyst G

Al$_2$O$_3$ (D 10-11 ®, BASF) is impregnated with a Pd-nitrate solution. The Pd content is 0.47% by weight.

Catalyst H

Catalyst H comprises an Al$_2$O$_3$/MgO carrier impregnated with a Pd-nitrate solution. Catalyst H contains 1.12% by weight of Pd, 19.8% by weight of MgO and 78.1% by weight of Al$_2$O$_3$.

Catalyst I

Catalyst I is prepared like catalyst F, except that the carrier material used is Al$_2$O$_3$ (D 10-11 ®, BASF). The Pd content is 0.5% by weight, and the PrO$_2$ content 5.0% by weight.

TABLE 1

| Example | 1 | 2 | 3 | 4 | 5 | 6 | 7 | 8 | 9 | 10 |
|---|---|---|---|---|---|---|---|---|---|---|
| Catalyst | A | A | B | C | D | E | F | G | H | I |
| Temperature | 350° C. | 400° C. | 375° C. | 350° C. | 375° C. | 375° C. | 375° C. | 375° C. | 375° C. | 375° C. |
| WHSV | 2.5 h$^{-1}$ | 2.5 h$^{-1}$ | 2 h$^{-1}$ | 2 h$^{-1}$ | 2 h$^{-1}$ | 2 h$^{-1}$ | 2 h$^{-1}$ | 2 h$^{-1}$ | 2 h$^{-1}$ | 2.5 h$^{-1}$ |
| H$_2$:educt, molar | 8:1 | 8:1 | 15:1 | 10:1 | 10:1 | 10:1 | 10:1 | 10:1 | 10:1 | 8:1 |
| Conversion % | 98.1 | 100 | 99.5 | 100 | 100 | 100 | 100 | 100 | 71.1 | 97.8 |
| Selectivity Methyl isopropyl ketone | 97.1 | 96.4 | 75.8 | 98.9 | 94.9 | 98.6 | 82.2 | 46.9 | 62.7 | 5.5 |
| Methyl isopropenyl ketone | 1.4 | 0.4 | 22.5 | 0.5 | 0.3 | / | 9.4 | 31.8 | 14.9 | 76.2 |

We claim:

1. A process for preparing a ketone of the formula I

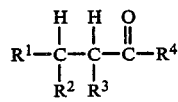

(I)

where R$^1$ to R$^3$ are each hydrogen and R$^1$ to R$^4$ are each alkyl of 1 to 12 carbon atoms, cycloalkyl of 4 to 8 carbon atoms, aryl, aralkyl or alkylaryl, each of which in turn may be substituted, or R$^1$ and R$^2$, or R$^2$ and R$^3$ together with the carbon atoms to which they are bonded may form a cycloalkane, wherein a ketone of the formula II

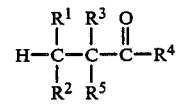

(II)

where R$^5$ is hydroxyl, alkoxy or carboxyl and the remaining radicals R$^1$ to R$^4$ have the above meanings, is reacted with hydrogen in the presence of an acid catalyst selected from the group consisting of zeolites of the pentasil type supporting one or more hydrogenation components.

2. The process of claim 1, wherein the hydrogenation component used is a transition metal and/or noble metal or a mixture thereof.

3. The process of claim 1, wherein the catalyst used contains a hydrogenation component and has been doped with an alkali metal, alkaline earth metal or rare earth.

4. The process of claim 1, wherein the reaction is carried out in a gas phase.